(12) United States Patent
Corma Canos et al.

(10) Patent No.: US 7,087,779 B2
(45) Date of Patent: Aug. 8, 2006

(54) ALDEHYDE CONVERSION METHOD USING A MOLECULAR SIEVE AND THE USE OF THE MOLECULAR SIEVE AS A CATALYST IN SAID METHOD

(75) Inventors: Avelino Corma Canos, Valencia (ES); María Mifsud Grau, Valencia (ES); Sara Iborra Chornet, Valencia (ES); Michael Renz, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 154 days.

(21) Appl. No.: 10/932,564

(22) Filed: Sep. 2, 2004

(65) Prior Publication Data

US 2005/0113604 A1    May 26, 2005

Related U.S. Application Data

(63) Continuation of application No. PCT/ES03/00093, filed on Feb. 27, 2003.

(30) Foreign Application Priority Data

Mar. 4, 2002    (ES) .................................. 200200598

(51) Int. Cl.
*C07D 331/02* (2006.01)
*C07D 301/12* (2006.01)
*C07C 69/76* (2006.01)

(52) U.S. Cl. ........................................ 560/64; 549/531
(58) Field of Classification Search ................. 560/64, 560/1; 549/531
See application file for complete search history.

(56) References Cited

FOREIGN PATENT DOCUMENTS

| | | |
|---|---|---|
| DE | 287 482 A5 | 10/1983 |
| EP | 1 010 667 A1 | 6/2000 |
| JP | 8 151343 | 11/1996 |
| RO | 105090 | 11/1994 |
| WO | WO 01/81291 A2 | 11/2002 |

OTHER PUBLICATIONS

Krow, GR, The Baeyer-Villiger Oxidation of Ketones and Aldehydes, 1993, Organic Reactions, Inc., vol. 43, p. 251-353; 773-797.
Godfrey, IM, etal, Preparation of Methoxyphenols by Baeher-Villiger Oxidation of Methoxybenzaldehydes, 1974, J.Chem. Soc. Perkin Trans. 1, pp. 1353-1354.
Anoune, N, etal., Use of Theoretical Chemistry To Explain Baeyer-Villiger Oxidations of Methoxy Aromatic Aldehydes, 1998, Jour of Chem Edu, vol. 75, No. 10, pp. 1290-1293.
Syper, L, The Baeyer-Villiger Oxidation of Aromatic Aldehydes and Ketones with Hydrogen Peroxide Catalyzed by Selenium Compounds. A Convenient Method for the Peparation of Phenols, 1989, Synthesis, pp. 167-172.
Matsumoto, M, etal., Acid-Catalyzed Oxidation of Benzaldehydes to Phenols by Hydrogen Peroxide, 1984, Amer. Chem. Soc., pp. 4740-4741.
Dodd, RH., etal, The Oxidation of Aromatic Aldehydes to Carboxylic Acids Using Hydrogen Peroxide in Formic Acid, 1993, Synthesis, pp. 295-297.
Renz, M., etal., Selective Baeyer-Villiger Oxidations of Aromatic Aldehydes and Cyclic Ketones with Sn-Beta Zeolites and $H_xO_2$, 2002, Chem. Eur. J., V.8, No. 20, pp. 4708-4717.
Chaudhari, K, etal., Synthesis, Characterization, and Catalytic Properties of Mesoporous Tin-Containing Analogs of MCM-41, 1999, Jour. Of Catalysis, V. 183, No. 2, pp. 281-291.
Corma, A., etal., Sn-MCM-41-a heterogeneous selective catalyst for the Baeyer-Villiger oxidation with hydrogen peroxide†e, 2001, Chem.Commun, V. 21, pp. 2190-2191.

*Primary Examiner*—Samuel A Barts
*Assistant Examiner*—Lalitha Nagubandi
(74) *Attorney, Agent, or Firm*—Klauber & Jackson LLC

(57) ABSTRACT

The invention relates to an aldehyde conversion method comprising putting an aldehyde into contact with oxygenated water and with a catalyst, under oxidation conditions, wherein the catalyst is a molecular sieve with pores of a diameter of at least 0.52 nm and has an empirical formula in a calcined and dehydrated form of $$(Sn_xTi_ySi_{1-x-y-z}Ge_z)O_2$$

wherein x is a molar fraction of the tin and has a value between 0.001 and 0.1; y is a molar fraction of titanium and has a value from zero to 0.1; and z is the molar fraction molar of the germanium and has a value from zero to 0.08.

20 Claims, No Drawings

ALDEHYDE CONVERSION METHOD USING A MOLECULAR SIEVE AND THE USE OF THE MOLECULAR SIEVE AS A CATALYST IN SAID METHOD

RELATED APPLICATIONS

The present application is a Continuation of co-pending PCT Application No. PCT/ES03/00093, filed Feb. 27, 2003, which in turn, claims priority from Spanish Application Serial No. 200200598, filed on Mar. 4, 2002. Applicants claim the benefits of 35 U.S.C. §120 as to the PCT application and priority under 35 U.S.C. §119 as to said Spanish application, and the entire disclosures of both applications are incorporated herein by reference in their entireties.

FIELD OF THE INVENTION

The present invention belongs to the field of conversion processes, by means of oxidation, of aldehyde into esters, acids and the hydrolysis products of the esters using a catalyst and aqueous $H_2O_2$ as oxidizer and the use of molecular sieves in such conversion processes.

BACKGROUND OF THE INVENTION

The substituted phenols, especially the derivatives with a 4-alcoxy substituent, are important substances in organic chemistry because they are intermediate products for the manufacture of medicines, agrochemicals and dyes. They are useful as polymerization inhibitors for vinyl-type monomers and polyester stabilizers as well as antioxidants for food and cosmetics also. There is considerable interest due to the synthesis of such products in industry and academy. See, for example Caproiu, M. T.; Banciu, A. A.; Olteanu, E. RO 105090, 1994; Saito, T.; Hirayama, T.; Sakagushi, S. JP 08151343, 1996; Schwabe, K.; Redslob, J.; Breitfeld, D.; Zeisig, R.; Tschiersch, B.; Wohlrab, W.; Wozniak, K. D.; Bayer, C.; Nowak, C.; et al. DD 287482, 1991. A strategy for the synthesis of these phenols consists in the Baeyer Villiger reaction with the corresponding aldehydes (Krow G. Org. React. 1993, 43, 251).

In general, this reaction is carried out using organic peracids as oxidizing agents. Meta-chloroperbenzoic acid (Godfrey, I. M.; Sargent, M. V.; Elix, J. A. J. Chem. Soc. Perkin Trans. 1 1974, 1353–1354.), as well as monopersuccinic acid (Anoune, N.; Hannachi, H.; Lanteri, P.; Longeray, R.; Arnaud, C. J. Chem. Ed. 1998, 75, 1290–1293.) gave good to excellent yields of the corresponding phenol in the case of the ortho-anisaldehyde and the para isomer. The meta-anisaldehyde transforms predominantly into meta-anisic acid. The disadvantage of an organic peracid like oxidizer is that it implies high costs and safety measures during its storage and handling, and produces at least a molecule of acid as waste product.

Oxygenated aqueous water would be a good oxidizing agent since it is safer and produces only water as subproduct. Nevertheless, it is not sufficiently reactive and needs activation by a catalyst. Activation may be achieved by selenium catalysts, and thus 4-methoxyphenol may be obtained from the corresponding aldehyde with an excellent yield (Syper, L. Synthesis 1989, 167–172). Nevertheless, in this case considerable quantities of catalyst are necessary, which have to be recovered and recycled or rejected, since only 12 cycles per active centre per 30 hours of reaction time are obtained.

The oxidation of aldehydes with $H_2O_2$ may also be catalyzed by Bronsted acids. The oxygenated water, activated by the sulphuric acid in methanol as solvent produces 4-methoxyphenol with an excellent yield. Nevertheless, anhydrous conditions and highly concentrated oxygenated water are necessary for this since it is considered that the reaction goes ahead via the peroxyhemiacetal that is unstable in the presence or water (Matsumoto, M.; Kobayashi, H.; Hotta, Y. J. Org. Chem. 1984, 49, 4740–4741). These anhydrous conditions of the reaction lead to extra costs in safety measures since the concentrated oxygenated water is potentially explosive.

On the other hand, the oxidation of Baeyer Villiger with oxygenated water in formic acid is less suitable for the production of phenols since it has been developed for the general oxidation of aldehydes to carboxylic acids (Dodd, R. H.; Le Hyaric, M. Synthesis 1993, 295–297). The present invention has as its main aim to overcome the disadvantages of the above-mentioned method by means of a method wherein the use of oxygenated water as oxidizing agent and the use of catalysts that give high conversions and are easily recyclable is permitted and that, besides, allows by simply changing the conditions of reaction, the possibility to choose as main final product different products as for example aryl formiate or substituted phenol.

DESCRIPTION OF THE INVENTION

The present invention achieves the above-mentioned objects by means of a method for the conversion of aldehydes that comprises putting an aldehyde, such as 4-methoxybenzaldehyde, 2-methoxybenzaldehyde, 4-propoxybenzaldehyde, 4-methylbenzaldehyde, benzaldehyde and 3,4-dimethoxybenzaldehyde, into contact with oxygenated water and with a catalyst under oxidation conditions, the method being characterized in that the catalyst is a molecular sieve with pores of a diameter of at least 0.52 nm and has an empirical formula in a calcined and dehydrated form of

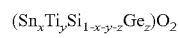

$$(Sn_xTi_ySi_{1-x-y-z}Ge_z)O_2$$

wherein x is a molar fraction of the tin and has a value between 0.001 and 0.1;

y is a molar fraction of titanium and has a value from zero to 0.1; and z is the molar fraction of the germanium and has a value from zero to 0.08.

This method can be carried out at a temperature between 20° C. and 150° C. and during a contact time between 10 minutes and 24 hours. The molar relationship of oxygenated water to aldehyde can be considered at between 0.1 and 3.

In accordance with the method of the present invention, aldehydes may be converted into formiates or acids. In particular, the method allows aromatic aldehydes to be converted into aryl formiates and/or directly into the hydrolysis products that are formic acid and a phenol with substituents. Changing the conditions of the reaction, the ester may be saponified during the process into the corresponding alcohol.

Suitable molecular sieves that can be used as catalysts in the method are molecular sieves corresponding to the general formula specified above wherein z and y have the value zero. In the same way, molecular sieves may be used that correspond to the above mentioned general formula, which show an X-ray diffractogram corresponding to a Beta zeolite.

Molecular sieves based on zeolites with pores, made up by rings with 12 or more tetrahedrons, as for example Beta zeolite and that contain tin are especially suitable as catalysts in the reaction described above. These molecular sieves have a three-dimensional microporous structure with at least tetrahedral units of $SiO_2$ and $SnO_2$, and from the crystallographic point of view have a regular system of pore or pores.

Also ordered mesoporous molecular sieves encompassed by the general formula defined above, as for example those with an MCM-41 structure are usable, wherein the y value as well as the z value may be zero or with an MCM-48 structure, or HMS or SBA-15 structure.

The present invention also refers to a method to use a molecular sieve with pores of a diameter of at least 0.52 nm and has an empirical formula in a calcined and dehydrated form of

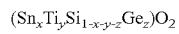

$(Sn_xTi_ySi_{1-x-y-z}Ge_z)O_2$ wherein
x is a molar fraction of the tin and has a value between 0.001 and 0.1;
y is a molar fraction of titanium and has a value from zero to 0.1; and
z is the molar fraction of the germanium and has a value from zero to 0.08;

in which method the above mentioned molecular sieve is used as catalyst in a conversion reaction of an aldehyde in the presence of oxygenated water to obtain a reaction product selected among the esters corresponding to the above mentioned aldehyde, acids corresponding to said aldehyde and phenols as hydrolysis products of the corresponding ester. The conditions of the method and the specific molecular sieves used in accordance with this method may be those previously described in relation to the characteristics of the method of the present invention.

The molecular sieves that may be used in accordance with the present invention can be prepared by means of a hydrothermal crystallization process in which a reaction mixture is prepared combining the sources of tin, silicon, a organic structure directing agent, optionally germanium, optionally titanium, optionally oxygenated water and water. Silicon sources include, though they are not limiting, colloidal silica, amorphous silica, pyrogenic silica, silica gel and tetraalkylorthosilicate. Tin sources include tin halides, tin alcoxides, tin oxides, metallic tin, alkaline stannates, alkaline-terreous stannates and organometallic tin compounds, without these being limiting examples. A preferred source is tin tetrachloride. Examples of tin alkoxides include tin buthoxide, tin ethoxide and tin propoxide. The organic structure directing agents include tetraalkylammonium ions such as the tetraethylamonium ion, aza-polycyclic compounds such as 1,4-diazabicyclo-[2,2,2]-octane; dialkyldibenzylammonium ions such as the dimethyl-dibenzylammonium ion and bispiperidinium ions, such as the 4,4'-trimethylene-bis-(N-benzyl-N-methylpiperidinium), without these being limiting. These ions may be used as hydroxides or halides. Germanium sources include germanium halides, germanium alkoxides and germanium oxides, without these being limiting. Finally, the sources of titanium include titanium alkoxides and titanium halides. The titanium alkoxides preferred are titanium tetraethoxide, titanium isopropoxide and titanium tetrabuthoxide.

Hydroxide or fluoride ions are used as $SiO_2$ mobilizing agents. The synthesis is carried out in a hydrothermal system at temperatures between 120 and 195° C. and during times between 12 hours and 25 days. Once the material has crystallized, the solids are separated from the liquids, and the solids are washed with water up to around 9 pH. Finally the dry solid is calcined in air or in $N_2$ followed by air at temperatures between 400 and 700° C. in order to eliminate the organic component.

A molecular sieve preferred corresponds to that of the Beta zeolite and its possible individual or combined polymorphs. In the case of the Beta zeolite, the X-ray diffractogram shows at least the peaks and intensities presented in Table A. The intensities shown in Table A are relative intensities that are obtained relating the intensity of each peak (1) with that of the darkest line ($1_0$). The intensity is calculated by means of the equation $100 \times 1/1_0$ and is represented by vs, s, m and w, where these are defined as: vs=80–100; s=60–80; m=15–60 and w=0–15.

TABLE A

| θ | d (Å) | Relative intensity |
|---|---|---|
| 7.22 | 12.23 | m |
| 7.76 | 11.38 | s |
| 21.54 | 4.12 | m |
| 22.57 | 3.94 | vs |
| 22.96 | 3.87 | w |
| 25.45 | 3.50 | w |
| 27.00 | 3.30 | w |
| 29.00 | 3.08 | w |
| 29.65 | 3.01 | m |
| 30.60 | 2.92 | w |

The synthesized zeolite is activated for adsorption or catalytic reactions generally through calcination of the molecular sieve at a temperature between 300° C. and 1000° C. during a time generally between 1 and 10 hours. As has been said, the molecular sieves described above perform very well as catalysts for the oxidation of aldehydes to formiates or acids, or to ester hydrolysis products. Examples of aldehydes that can be used in the process include aliphatic aldehydes, α,β-unsaturated aldehydes, and aromatic aldehydes, without being limiting. Specific examples are 2-methoxybenzaldehyde, 4-methoxybenzaldehyde, 4-methylbenzaldehyde, benzaldehyde, 4-npropoxybenzaldehyde and 3,4-dimethoxybenzaldehyde.

The process implies putting the aldehyde in contact with a catalyst (as is described above) and oxygenated water under oxidation conditions. The oxidation conditions for the instantaneous process include a temperature between 20 and 150° C. and a contact time between 10 min. and 24 hours. As has been pointed out previously, oxygenated water is used as oxidizing agent in a solution in water of 3% to 70% in weight, preferably a solution at 35% in weight. This reaction may be carried out with or without solvent. In the case where the use of a solvent is desired, preferred solvents are acetonitrile, dioxane, and toluene. Likewise, the process may be carried out in a batch type or continuous reactor. When operating in batch mode, the catalyst, the aldehyde, optionally a solvent, and the $H_2O_2$ are mixed in a suitable reactor preferably stirring the mixture at the desired temperature during a time between 10 minutes and 24 hours. The $H_2O_2$/aldehyde molar relationship may vary between 3 and 0.1 and preferably between 1 and 0.3. In continuous mode, the catalyst may be used on a fixed bed, boiling bed, mobile bed, or in any other known configuration. When a fixed bed is used, the aldehyde and oxygenated water may pass from a downwards to upwards direction or vice versa with regard to the catalytic bed. The $H_2O_2$ and the aldehyde can be injected separately, or they can be mixed before, and afterwards injected into the reactor.

Regardless of the way the reagents are introduced and the type of bed used, the reagents flow through the reactor at a spatial speed between 0.01 and 50 h$^{-1}$ to ensure the suitable contact time between the reagents and the catalyst. Finally, regardless of whether batch mode or a continuous process is used, the products, the reagents and any formed by-product are separated by methods well known in the art.

EMBODIMENTS OF THE INVENTION

The following examples intend to illustrate characteristics related to the invention.

EXAMPLES

Example 1

Preparation of Seeds for the Beta Zeolite Used for the Preparation of a Beta Zeolite with Sn In a reactor, 1.85 grams of AlCl$_3$.6H$_2$O were dissolved in 4.33 grams of water. 45.24 grams of tetraethylamonium hydroxide (TEAOH) (aqueous solution of 35% in weight) were added to this solution. Afterwards, 40 grams of tetraethylortosilicate (TEOS) were added and the mixture was stirred until the ethanol formed by the hydrolysis of the TEOS had evaporated. The final composition of the gel was the following:

SiO$_2$:0.28TEA$_2$O:0.02Al$_2$O$_3$:6.5H$_2$O

The obtained solution was transferred to a stainless steel autoclave with inner walls protected by Teflon©, heated to 140° C. and left to react for 3 days with stirring. The product was recovered by centrifugation, washed with distilled water and dried to 100° C. The product showed the Beta zeolite structure with crystallinity near to 90%.

The sample of the Beta zeolite in the previous paragraph was dealuminated by treating 1 gram of the zeolite with 60 grams of HNO$_3$ (60% in weight) at 80° C. for 24 hours. The solid was recovered by filtration, washed with water and dried at 100° C. The crystallinity of this product was 70% and the Si/Al relationship was determined by elementary analysis and was larger than 2000.

Example 2

Synthesis of a Tin Silicate with the Structure of a Beta Zeolite 30 grams of TEOS and 32.99 grams of TEAOH (35% in weight) were mixed in a reactor. After 90 minutes, a solution of 0.43 grams of SnCl$_4$.5H$_2$O (98%) was added in 2.75 grams of water and the mixture was stirred until evaporation of the ethanol formed by the hydrolysis of the TEOS. 3.2 grams of fluorhydric acid were added to the bleached solution (48% in weight) and a viscous paste was obtained. Finally, a suspension of 0.36 grams of Beta zeolite dealuminated seeds, prepared according to Example 1 was added to 1.75 grams of water. The final composition of the gel is shown by the following formula:

SiO$_2$:0.27TEAO:0.008SnO$_2$:0.54HF:7.5H$_2$O

The paste was transferred to an autoclave of stainless steel with inner walls protected by Teflon©, heated to 140° C. and left to react during 11 days with stirring. After 11 days the product was recovered by filtration. By means of X-ray diffraction, it was demonstrated that the product had the structure of a Beta zeolite with crystallinity near to 95%. The elementary analysis gave a tin content with 1.62% by weight. The product was calcined at 580° C. for 3 hours and maintained its crystallinity. The empirical formula of the calcined, anhydrous material was the following:

(Si$_{0.992}$Sn$_{0.008}$)O$_2$

This product was named sample A.

Example 3

Synthesis of a Pure Beta Zeolite Silica 30 grams of TEOS and 32.99 grams of TEAOH (35% in weight) were mixed in a reactor. The mixture was stirred until the evaporation of the ethanol formed by the hydrolysis of the TEOS. 3.2 grams of fluorhydric acid (48% in weight) were added to the solution and a viscous paste was obtained. Finally, a suspension of 0.36 grams of Beta zeolite dealuminated seeds prepared according to Example 1 was added to 1.75 grams of water. The final composition of the gel is shown by the following formula:

SiO$_2$:0.27TEA$_2$O:0.54HF:7.5H$_2$O

The paste was transferred to an autoclave of stainless steel with inner walls protected by Teflon©, heated to 140° C. and left to react during 24 hours with stirring. After 24 hours the product was recovered by filtration. By means of X-ray diffraction, it was demonstrated that the product had the structure of a Beta zeolite with a crystallinity near to 100%. The product was calcined at 580° C. for 3 hours and maintained its crystallinity.

This product was named sample C.

Example 4

Synthesis of a Tin Silicate Mesoporous Molecular Sieve

A hexa-decyl-trimethylamonium hydroxide (C$_{16}$TAOH) aqueous solution, a tetramethylamonium hydroxide solution and an aqueous SnCl$_4$.5H$_2$O solution were mixed in a reactor. After obtaining a homogeneous solution the silica was added by constant stirring. The final composition was the following:

1SiO$_2$:0.16C$_{16}$TAOH:0.26TMAOH:0.04SnCl$_4$:24.3H$_2$O

The homogeneous gel was transferred to an autoclave of stainless steel with inner walls protected by Teflon©, heated to 135° C. and left to react during 24 hours without stirring. The resultant product was recovered by filtration, washed and dried for 24 hours at 60° C. The occluded organic was eliminated by heating the solid at 540° C. during an hour in nitrogen flow and afterwards for 6 hours in air. The obtained solid shows a typical MCM-41 structure model in X-ray diffraction. Elementary analysis gave a tin content of 7.1% in weight. The empirical formula of the calcined, anhydrous material was:

$(Si_{0.96}Sn_{0.04})O_2$

This product was named sample D.

Example 5

Sample B is a commercial zeolite supplied by Zeolyst with the VALFOR CP811BL-25 (Si/Al=13)code. The samples of A to D were tested for the selective oxidation of 4-methoxybenzaldehyde to 4-methoxyphenyl formiate and the corresponding hydrolysis products 4-methoxyphenol and formic acid according to the following procedure. In a flask, 50 mg of catalyst were added to a 0.5 g aldehyde solution, aqueous oxygenated water (35% in weight) in small excess (1.5 equivalents) and dioxane (3.0 g) as solvent. The flask was heated to 80° C. and after 7 hours the conversion and the selectivity to 4-methoxyphenyl formiate (1a) and 4-methoxyphenol (2a) were determined. The activities and selectivities obtained for the conversion of 4-methoxybenzaldehyde with several catalysts are shown in Table 1.

TABLE 1

Oxidation of 4-methoxybenzaldehyde with several catalysts

| Catalyst | conv. [%] | distribution of products 1a | 2a | other |
|---|---|---|---|---|
| A (Sn-Beta) 2% $SnO_2$ | 49 | 63 | 35 | 2 |
| B (Al-Beta) 3% $Al_2O_3$ | 17 | 77 | 23 | 0 |
| C (Beta) $SiO_2$ | 0 0 | — | — | — |
| D (Sn-MCM-41) 9% $SnO_2$ | 25 | 45 | 42 | 13 |

Example 6

Catalyst A was tested by means of the procedure described in Example 5 with 4-methoxybenzaldehyde and aqueous oxygenated water with 50% by weight (1.4 equivalents) in dioxane (3.0 g) or in acetonitrile (3.0 g) as solvent. The obtained results are shown in Table 2.

TABLE 2

Oxidation of 4-methoxybenzaldehyde in dioxane and acetonitrile using a Sn-Beta zeolite as catalyst (sample A)

| solvent | conv. [%] | distribution of products 1a | 2a | other |
|---|---|---|---|---|
| dioxane | 43 | 77 | 23 | 0 |
| MeCN | 57 | 4 | 96 | 0 |

Example 7

Catalyst A was tested by means of the procedure described in Example 6 with 4-n-propoxybenzaldehyde, with 4-methylbenzaldehyde and with benzaldehyde. After 7 hours the conversion and selectivity to the corresponding arylic formiate (1) and substituted phenol (2) and to the corresponding aromatic acid (3) were determined. These results are shown in Table 3.

TABLE 3

Oxidation of various aldehydes using an Sn-Beta zeolite as catalyst (sample A)

| substrate | solvent | conv. [%] | Distribution of products 1 | 2 | 3 | others |
|---|---|---|---|---|---|---|
| 4-methoxy- | dioxane | 43 | 77 | 23 | 0 | 0 |
| 4-methoxy- | MeCN | 57 | 4 | 96 | 0 | 0 |
| 4-n-propoxybenzaldehyde | dioxane | 62 | 77 | 23 | 0 | 0 |
| 4-n-propoxybenzaldehyde | MeCN | 82 | 13 | 87 | 0 | 0 |
| 4-methyl- | dioxane | 26 | 29 | 44 | 23 | 4 |
| 4-methyl- | MeCN | 22 | 2 | 18 | 35 | 16 |
| benzaldehyde | dioxane | 8 | 0 | 0 | 100 | 0 |
| benzaldehyde | MeCN | 19 | 0 | 0 | 100 | 0 |

Example 8

Catalyst A was tested by means of the procedure described in Example 5 with 2-methoxybenzaldehyde at 90° C. After 7 hours, a conversion of 24% and a selectivity of 60% for 2-methoxyphenyl formiate (1e) was observed and a selectivity of 25% for 2-methoxyphenol (2e).

Example 9

Catalysts A y D were tested by means of the procedure explained in Example 5 with 3,4-dimethoxybenzaldehyde at 90° C. The activity and selectivity of both catalysts for the conversion of the 3,4 dimethoxybenzaldehyde into 3,4-dimethoxyphenyl formiate (1f) and 3,4-dimethoxyphenol (2f) are shown in Table 4.

TABLE 4

Oxidation of 3,4-dimethoxybenzaldehyde using samples A y D as catalysts

| Catalyst | conversion [%] | Distribution of products 1f | 2f | others |
|---|---|---|---|---|
| A (Sn-Beta) 2% $SnO_2$ | 9 | 92 | 0 | 8 |
| D (Sn-MCM-41) 9% $SnO_2$ | 22 | 97 | 0 | 3 |

Example 10

Catalyst A for the selective oxidation of 4-methoxybenzaldehyde without solvent was tested according to the following procedure. In a flask, 50 mg of catalyst were added to 3.0 g of aldehyde solution and 0.29 grams of aqueous oxygenated water (35% in weight). The flask was heated to 80° C. and after an hour a 91% conversion with regard to the oxygenated water and a selectivity of 97% for the 4-methoxyphenyl formiate (1a) and a selectivity of 2% for the 4-methoxyphenol (2a) was observed.

The invention claimed is:

1. A method for the conversion of aldehydes comprising putting an aldehyde into contact with oxygenated water and with a catalyst, under oxidation conditions, wherein the catalyst is a molecular sieve with pores of a diameter of at least 0.52 nm and has an empirical formula in a calcined and dehydrated form of

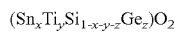

wherein
- x is a molar fraction of the tin and has a value between 0.001 and 0.1;
- y is a molar fraction of titanium and has a value from zero to 0.1; and
- z is the molar fraction of the germanium and has a value from zero to 0.08.

2. A method according to claim 1, characterized in that the molecular sieve has a crystalline structure with an X-ray diffractogram corresponding to a Beta zeolite.

3. A method according to claim 1, characterized in that it is carried out at a temperature between 20° C. and 150° C. and during a contact time between 10 minutes and 24 hours.

4. A method according to claim 1, characterized in that it is carried out at a molar relationship of oxygenated water to aldehyde between 0.1 and 3.

5. A method according to claim 1, characterized in that the aldehyde is selected from the group formed by 4-methoxybenzaldehyde, 2-methoxybenzaldehyde, 4-propoxybenzaldehyde, 4-methylbenzaldehde, benzaldehyde and 3,4-dimethoxybenzaldehyde.

6. A method according to claim 1, characterized in that z and y have a zero value.

7. A method according to claim 1, characterized in that the molecular sieve is an ordered mesoporous molecular sieve.

8. A method according to claim 1, characterized in that the molecular sieve is an ordered mesoporous molecular sieve with an MCM-41 structure.

9. A method according to claim 1, characterized in that the molecular sieve is an ordered mesoporous molecular sieve with an MCM-41 structure, and the y value as well as the z value is zero.

10. A method according to claim 1, characterized in that the molecular sieve is an ordered mesoporous molecular sieve with an MCM-48 structure.

11. A method according to claim 1, characterized in that the molecular sieve is an ordered mesoporous molecular sieve with an HMS structure.

12. A method according to claim 1, characterized in that the molecular sieve is an ordered mesoporous molecular sieve with an SBA-15 structure.

13. A method to use a molecular sieve with pores of a diameter of at least 0.52 nm that has an empirical formula in a calcined and dehydrated form of

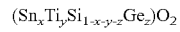

wherein
- x is a molar fraction of the tin; and it has a value between 0.001 and 0.1;
- y is a molar fraction of titanium and has a value from zero to 0.1; and
- z is the molar fraction of the germanium and has a value from zero to 0.08;

wherein said molecular sieve is used as catalyst in a conversion reaction of an aldehyde in the presence of oxygenated water to obtain a reaction product selected among the esters corresponding to said aldehyde, acids corresponding to the said aldehyde, and phenols as hydrolysis products of the corresponding ester.

14. A method according to claim 13, wherein the molecular sieve is used as catalyst in a reaction of an aldehyde selected from the group formed by 4-methoxybenzaldehyde, 2-methoxybenzaldehyde, 4-propoxybenzaldehyde, 4-methylbenzaldehyde, benzaldehyde and 3,4-dimethoxybenzaldehyde.

15. A method according to claim 13, characterized in that at least one of z and y has a zero value in the molecular sieve.

16. A method according to claim 13, characterized in that the molecular sieve is used in an oxidation reaction that is carried out at a temperature between 20° C. and 150° C. during a contact time between 10 minutes and 24 hours.

17. A method according to claim 13, characterized in that the molecular sieve is used in a reaction that is carried out at a molar relationship of oxygenated water to aldehyde between 0.1 and 3.

18. A method according to claim 13, characterized in that the molecular sieve has a crystalline structure with the X-ray diffractogram corresponding to a Beta zeolite.

19. A method according to claim 13, characterized in that the molecular sieve is an ordered mesoporous molecular sieve.

20. A method according to claim 19, characterized in that the ordered mesoporous molecular sieve is selected from the group formed by ordered mesoporous molecular sieves with an MCM-41 structure, ordered mesoporous molecular sieves with an MCM-41 structure where the y value as well as the z value is zero, ordered mesoporous molecular sieves with an MCM-48 structure, ordered mesoporous molecular sieves with an HMS structure, and ordered mesoporous molecular sieves with an SBA-15 structure.

* * * * *